(12) United States Patent
Stanton et al.

(10) Patent No.: US 6,744,848 B2
(45) Date of Patent: Jun. 1, 2004

(54) METHOD AND SYSTEM FOR LOW-DOSE THREE-DIMENSIONAL IMAGING OF A SCENE

(75) Inventors: Martin Stanton, Stowe, MA (US); Alexander Stewart, Waltham, MA (US); Walter Phillips, Arlington, MA (US)

(73) Assignee: Brandeis University, Waltham, MA (US)

( * ) Notice: Subject to any disclaimer, the term of this patent is extended or adjusted under 35 U.S.C. 154(b) by 186 days.

(21) Appl. No.: 09/781,787

(22) Filed: Feb. 12, 2001

(65) Prior Publication Data

US 2001/0038681 A1 Nov. 8, 2001

Related U.S. Application Data

(60) Provisional application No. 60/181,981, filed on Feb. 11, 2000.

(51) Int. Cl.[7] .............................................. G01B 15/02
(52) U.S. Cl. .............................. 378/55; 378/37; 378/62
(58) Field of Search ............................. 378/37, 55, 62, 378/64, 98.8, 98.9, 98.12

(56) References Cited

U.S. PATENT DOCUMENTS

| | | | |
|---|---|---|---|
| 4,303,860 A | 12/1981 | Bjorkhom et al. | 250/363 |
| 4,323,925 A | 4/1982 | Abell et al. | 358/213 |
| 4,445,117 A | 4/1984 | Gaalema et al. | 340/825.91 |
| 4,852,137 A | 7/1989 | Mackay | 378/62 |
| 4,970,398 A | 11/1990 | Scheid | 250/374 |
| 5,072,591 A | 12/1991 | Grange et al. | 62/50.7 |
| 5,142,557 A | 8/1992 | Toker et al. | 378/37 |
| 5,197,294 A | 3/1993 | Galvan et al. | 62/3.62 |
| 5,216,250 A | 6/1993 | Pellegrino et al. | 250/370.09 |

(List continued on next page.)

OTHER PUBLICATIONS

Hudson, H. M. and Larkin R. S., "Accelerated Image Reconstruction Using Ordered Subsets of Projection Data," IEEE Transactions on Medical Imaging, vol. 13, No. 4, 601–609 (1994).

Kamphuis, C. and Beekman, F. J., "Accelerated Iterative Transmission CT Reconstruction Using an Ordered Subsets Convex Algorithm" IEEE Transactions on Medical Imaging, vol. 17, No. 6, 1101–1105 (1998).

(List continued on next page.)

Primary Examiner—David V. Bruce
Assistant Examiner—Courtney Thomas
(74) Attorney, Agent, or Firm—Nutter McClennen & Fish LLP

(57) ABSTRACT

The present invention provides a system for imaging an object by irradiating it with low doses of radiation, such as x-ray, from a plurality of positions angularly distributed about the object, and analyzing the intensity of the radiation transmitted through the object. A system according to the invention can include a radiation source, a low noise detector, and an image processor. The radiation source emits radiation toward a target scene, containing an object to be imaged, from a plurality of angular positions. In one embodiment, the plurality of angular positions defines an arc about the target scene. In another embodiment, the radiation source moves in a series of steps of varying angular spacing along the arc to generate the multiple images of the scene. The detector is positioned to detect radiation transmitted through the scene and produces radiation transmission data representing the intensity of the radiation transmitted through the scene. The image processor receives the radiation transmission data from the detector and produces a three-dimensional image of the scene. In some embodiments of the invention, the resolution of the detector can be varied. In such embodiments, the system of the invention further includes a resolution controller that varies the spatial resolution of the detector in response to the angular position from which radiation is emitted toward the scene.

13 Claims, 13 Drawing Sheets

U.S. PATENT DOCUMENTS

| | | | |
|---|---|---|---|
| 5,235,184 A | 8/1993 | Paulson | 250/238 |
| 5,533,087 A | 7/1996 | Snoeren | 378/98.3 |
| 5,550,380 A | 8/1996 | Sugawara et al. | 250/370.11 |
| 5,550,386 A | 8/1996 | Kojima et al. | 250/588 |
| 5,551,244 A | 9/1996 | Bailey | 62/51.2 |
| 5,596,200 A | 1/1997 | Sharma et al. | 250/370.14 |
| 5,604,781 A | 2/1997 | Suzuki et al. | 378/62 |
| 5,617,461 A | 4/1997 | Schreiner | 378/98.5 |
| 5,693,948 A | 12/1997 | Sayed et al. | 250/370.09 |
| 5,852,646 A * | 12/1998 | Klotz et al. | 378/8 |
| 5,872,828 A | 2/1999 | Niklason et al. | 378/23 |
| 5,891,959 A | 4/1999 | Kunz | |
| 5,896,437 A | 4/1999 | Ploetz | 378/2 |
| 5,999,587 A * | 12/1999 | Ning et al. | 378/4 |
| 6,265,736 B1 * | 7/2001 | Dillen et al. | 257/232 |
| 6,618,468 B2 * | 9/2003 | Klotz et al. | 378/98.12 |

OTHER PUBLICATIONS

Lange, K. and Carson, R., "EM Reconstruction Algorithms for Emission and Transmission Tomography," Journal of Computer Assisted Tomography, vol. 8, No. 2, 306–316 (1984).

Lange, K. and Fessler, J.A., "Globally Convergent Algorithms for Maximum a Posteriori Transmission Tomography," IEEE Transactions on Image Processing, vol. 4, No. 10, (1995).

Lyon. R. G., et al., "A Maximum Entropy Method with a Priori Maximum Likelihood Constraints," The Astrophysical Journal, vol. 478, 658–662 (1997).

Manglost, S. H., et al., "Transmission Maximum–Likelihood reconstruction with Ordered Subsets for Cone Beam CT," Physics Medicine and Biology, vol. 40, 1225–1241n (1995).

Niklason, L. et al., "Digital Breast Tomosynthesis: Potentially a New Method for Breast Cancer Screening," Available FTP: www.azn.n./rrng/xray/digmam/iwdm98/abstracts/node40.html, (Dec. 1999).

Shepp, L. A. and Vardi, Y., "Maximum Likelihood Reconstruction for Emission Tomography," IEEE Transactions on Medical Imaging, vol. Mi–1, No. 2, 113–121 (1982).

Skilling, J. and Bryan, R. K., "Maximum Entropy Image Reconstruction: General Algorithm," Monthly Notices of the Royal Astronomical Society, vol. 211, 111–124 (1984).

Wu, N., "The Maximum Entropy Method," Springer Series in Information Sciences, vol. VII, 1–327 (1997).

The Astrophysical Journal, A Maximum Entropy Method with a Priori Maximum Likelihood Constraints, vol. 458, pp. 658–662, Apr. 1, 1997.

J. Shilling and R.K. Bryan, Maximum Entropy Image Reconstruction: General Algorithm, Mon.No. R. astr. Soc. vol. 211, 111–124, 1984.

IEEE Transactions on Medical Imaging, Accelerated Iterative Transmission CT Reconstruction Using an Ordered Subsets Convex Algorithm, vol. 17, No. 6, Dec. 1998.

Kenneth Lange and Richard Carson, EM Reconstruction Algorithms for Emission and Transmission Therapy, Journal of Computer Assisted Tomography, vol. 8(2), 306–316, Apr. 1984.

Kenneth Lange and Jeffrey A. Fessler, Globally Convergent Algorithms for Maximum a Posteriori Transmission Tomography, IEEE Transactions on Image Processing, vol. 4, No. 10, Oct. 1995.

Manglost et al., Transmission Maximum–likelihood Reconstruction with Ordered Subsets for Cone Beam CT, Phys. Med. Biol. vol. 40, 1225–1241, 1995.

L.A. Shepp and Y. Vardi, Maximum Likelihood Reconstruction for Emission Tomography, IEEE Transactions on Medical Imaging, vol. M1–1, No. 2, Oct. 1992.

\* cited by examiner

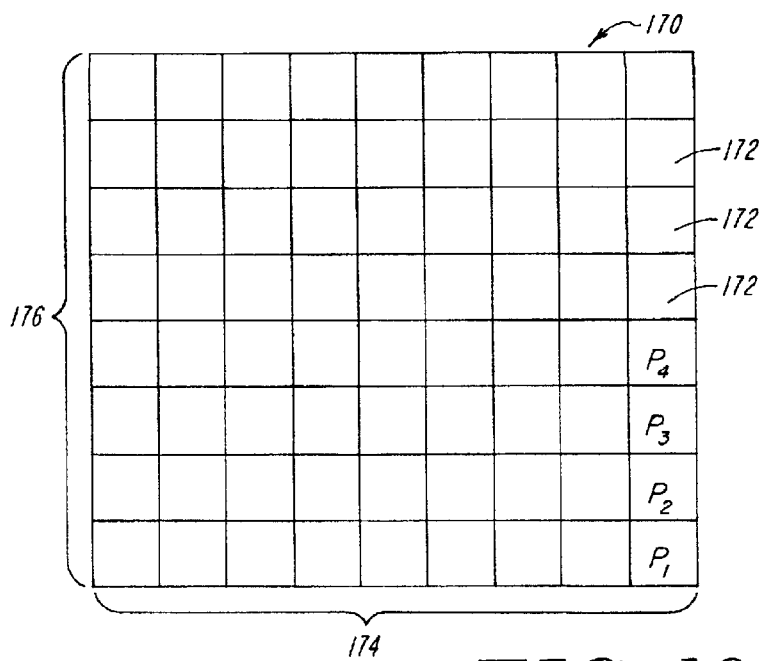
FIG. 10
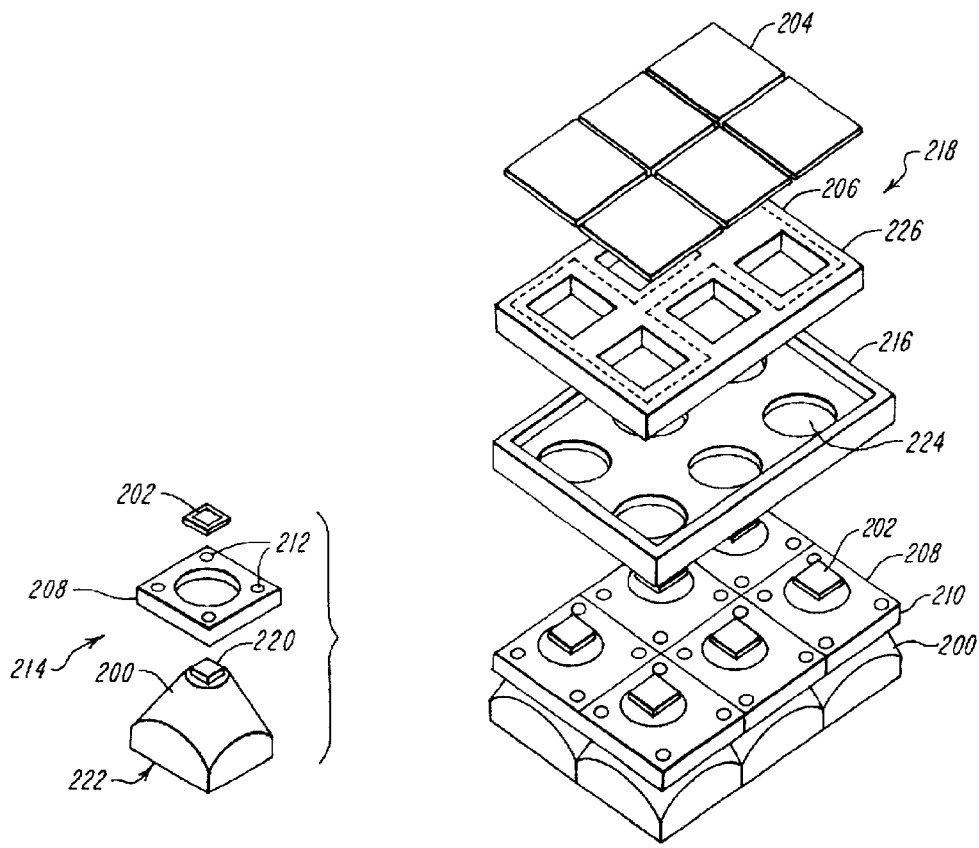
FIG. 11A   FIG. 11B

METHOD AND SYSTEM FOR LOW-DOSE THREE-DIMENSIONAL IMAGING OF A SCENE

CROSS-REFERENCE TO RELATED APPLICATIONS

This application claims priority from U.S. Provisional Patent Application No. 60/181,981 filed on Feb. 11, 2000.

STATEMENT REGARDING FEDERALLY SPONSORED RESEARCH

This invention was made with government support under Contract No. CA66232 awarded by the National Cancer Institute. The government has certain rights in the invention.

BACKGROUND OF THE INVENTION

The present invention relates generally to methods and systems for imaging a scene using a low dose of radiation and more specifically to method and system for generating a three-dimensional image of a body part using a low dose of x-ray radiation.

Systems that utilize high energy radiation, such as x-radiation and gamma radiation, to examine the internal structure of a solid object are known. Such systems typically irradiate an object under examination with high energy x-radiation or gamma radiation and utilize detection apparatus to measure the intensity of the radiation that is transmitted through the object.

It is known that these systems may be used to produce images of body parts. Detection systems, particularly those used for medical applications, such as mammography, direct x-rays through the body part of interest toward an x-ray detector. The x-ray detector receives x-rays transmitted through the body part and produces an image of the body part based on the intensity distribution of the x-rays incident on the detector.

In conventional x-ray mammography systems, two images of the breast are made. Each of the images are obtained at approximately right angles to each other. The purpose of obtaining images at two different angles is to increase the likelihood of seeing features in the breast that are not recognizable from one direction, but which may be discernable in another direction.

Conventional mammography techniques, however, have significant false negative and false positive rates that can result in either missing cancers in their early stages or in unnecessary surgical procedures. False results are due, in part, to the limitations of projecting a three-dimensional object into a two-dimensional image. In particular, structures at one level in the breast may partially or entirely obscure structures at another level, making identification of cancers difficult. In addition, the superimposition of normal structures at different levels may create an image that erroneously looks like a cancer. The overlapping of structures prevents visualization of a true representation of the breast and is referred to herein as structure noise. In addition, breast imaging using only two transmission images of a breast suffers from low contrast differences between normal and cancerous tissues.

One method for reducing structure noise is to perform a three-dimensional reconstruction of the breast using three-dimensional x-ray imaging, known as computed tomography (hereinafter "CT"). In conventional CT imaging, hundreds or thousands of x-ray images are recorded. These images are analyzed using computational methods to generate a three-dimensional image of the breast. The radiologist may separate the three-dimensional image into slices in order to separate the images of overlapping structures and better analyze the image. However, the number of images needed for conventional CT requires too high a dose of radiation to be used routinely on patients. High doses of radiation are required to obtain high-resolution three-dimensional images. CT techniques have not been applied to screening for breast cancer due to the prohibitive high doses of radiation that would be necessary to obtain breast images with diagnostically useful signal-to-noise ratios and high spatial resolution. Further, the time to collect the large number of images further prohibits use of this system on patients. Conventional CT systems are therefore not suitable for use on patients for screening mammography.

What is desired then is a system for imaging a patient's breast which generates a three-dimensional image of a breast which may be used to view different levels of the breast and which uses a total radiation dose that is comparable to the dose of a standard screening mammogram. What is also desired is a system which does not require a large amount of time to collect the images necessary to generate the three-dimensional image.

SUMMARY OF THE INVENTION

In one aspect, the invention relates to a system for imaging a scene using a low dose of radiation. The imaging system includes a radiation source, a variable spatial resolution detector, a resolution controller and an image processor. The radiation source is capable of emitting radiation toward a target scene from a plurality of angular positions, which can define, for example, an arc about the target scene In one embodiment, the radiation source is a source of x-ray radiation. In another embodiment, the radiation source moves in a series of steps of varying angular spacing along the arc to generate multiple images of the scene. The detector is positioned to detect radiation transmitted through the scene and produces radiation transmission data representing the intensity of the radiation transmitted through the scene. In one embodiment, the detector is a two-dimensional detector.

The resolution controller is in electrical communication with the detector and varies the spatial resolution of the detector in response to the angular position from which radiation is emitted by the radiation source toward the scene. The image processor receives the radiation transmission data from the detector and produces an image of the scene.

The invention also relates to a method for imaging a scene. The method includes the steps of irradiating a scene from a plurality of angular positions, detecting radiation transmitted through the scene at a plurality of different spatial resolutions, producing radiation transmission data representative of the intensity of the radiation transmitted through the scene at each of the plurality of angular positions, and producing a three-dimensional image of the scene.

In another aspect, the invention provides a system for imaging an object, which includes a movable radiation source that can direct radiation toward the object from a plurality of angular positions non-uniformly distributed about the object. The system further includes a detector movable about at least one axis so as to detect radiation transmitted through the object at each angular position of the source. The detected radiation provides radiation transmission data that an image processor can analyze to produce an image of the object. The non-uniformly distributed angular positions can define an arc about the object. Further, these angular positions can be selected to lie in a plane extending through approximately the center of the source and that of the object. Motion controllers coupled to the source and/or the detector can be utilized to move the source and/or the detector to various angular positions.

In a related aspect, the invention provides a method of an imaging an object. The method calls for irradiating the object from a plurality of non-uniformly distributed angular positions, and detecting the transmitted radiation at each position to create radiation transmission data. The image of the object is then constructed by analyzing the radiation transmission data.

The present invention has the advantage of producing a three-dimensional image of a scene using a total radiation dose which is comparable to or less than the dose used in conventional screening methods. The invention has the further advantage of requiring a smaller number of images than conventional CT, thus reducing the amount of time that a patient must remain stationary. In particular, the invention provides an improved method of performing clinical mammography that results in earlier diagnosis of breast cancer, fewer negative biopsies, decreased study time and fewer call backs after initial screening exams.

BRIEF DESCRIPTION OF THE DRAWINGS

This invention is pointed out with particularity in the appended claims. The above and further advantages of this invention may be better understood by referring to the following description taken in conjunction with the accompanying drawings, in which:

FIG. 10 is a diagram of an embodiment of a photodetector array according to the invention;

FIG. 11A is an exploded view of an embodiment of a sensor module according to the invention;

FIG. 11B is an exploded view of an embodiment of a detector according to the invention;

Like reference characters in the respective drawn figures indicate corresponding parts.

DETAILED DESCRIPTION OF THE INVENTION

Figure 1:
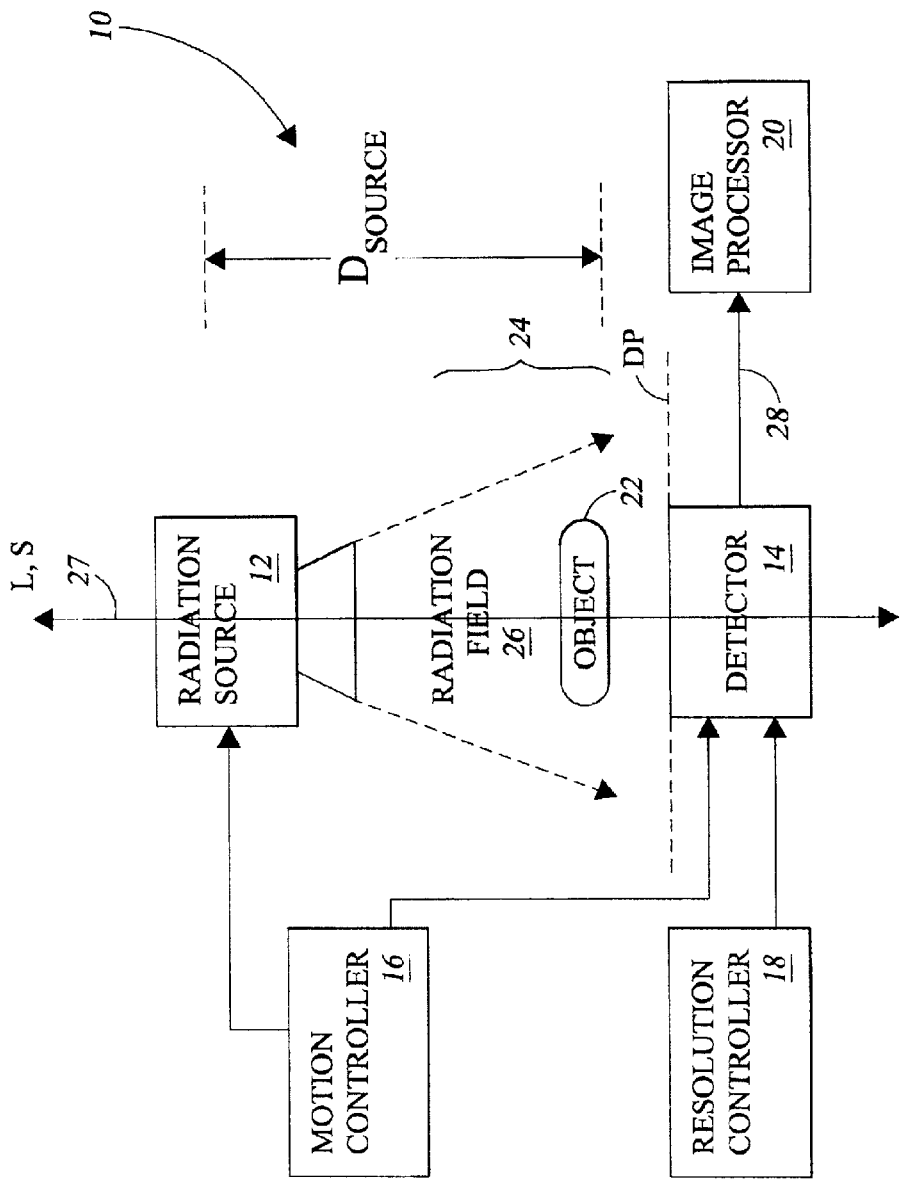
FIG. 1 is a schematic block diagram of an embodiment of an imaging system according to the invention.

In broad overview, and referring to FIG. 1, a block diagram of an embodiment of an imaging system 10 according to the present invention includes a radiation source 12, a detector 14, a motion controller 16, a resolution controller 18 and an image processor 20. The imaging system 10 can be used to image a single object 22 or a plurality of objects located within a target scene 24. The target scene 24 is the region in space between the radiation source 12 and the detector 14 to be imaged. The target scene 24 is located in the path of the radiation passing from the radiation source 12 to the detector 14. The target scene 24 may be the entire region of space located in the path of the radiation passing from the radiation source 12 to the detector 14 or only a predetermined portion of the space.

In one embodiment, the object 22 is a portion of a patient's body. In different embodiments, the components of the imaging system 10 may be configured to allow the patient to stand upright, to lie prone or to be oriented at any desired angular position. In one such embodiment, the imaging system 10 is an x-ray mammography system, and the object 22 is a patient's breast. The aspects of the imaging system 10 disclosed herein may be utilized in other detection and imaging systems which may be suitable for different applications. For example, embodiments of the imaging system 10 may be utilized in other medical imaging applications, scientific imaging applications such as x-ray crystallography, and industrial quality control applications.

The radiation source 12 emits radiation toward the target scene 24 and the object 22 to be imaged. In particular, the radiation source 12 emits radiation to form a radiation field 26. In one embodiment, the radiation source 12 is a source of x-ray radiation that generates a plurality of x-rays forming an x-ray radiation field 26. The object 22 is temporarily held motionless while it is exposed to the radiation field 26. Methods for holding the object 22 motionless will be described in detail below in the discussion of FIGS. 3 and 4.

The radiation source 12 is movable with respect to the stationary object 22 and is capable of emitting radiation toward the object 22 from a plurality of angular positions. In one embodiment, the radiation source 12 remains a predetermined distance $D_{SOURCE}$ from the object 12 as the radiation source 12 is moved to different angular positions with respect to the stationary object 22. In another embodiment, the distance $D_{SOURCE}$ may be varied as the radiation source 12 is moved to different angular positions. In the embodiment shown in FIG. 1, the motion controller 16 moves the radiation source 12 to the plurality of angular positions with respect to the object 22. In other embodiments, the radiation source 12 may be manually moved to different angular positions.

The detector 14 is positioned to receive the radiation that passes through the target scene 24 and the object 22. In one embodiment, the detector 14 is maintained at a predetermined position and in a predetermined orientation with respect to the radiation source 12. In one such embodiment, the predetermined position is located along a line L 27 that is perpendicular to the radiation source 12 and the detector 14 and that extends through the radiation source 12 and the detector 14. In another embodiment, the line L 27 passes through approximately the center of the radiation source 12 and the center of the detector 14. The center of the radiation source 12 is the center of the area from which the radiation source 12 emits radiation. The center of the detector 14 is the center of the area of the detector 14 capable of detecting radiation. In another embodiment, the position of the detector 14 with respect to the radiation source may be varied. The motion controller 16 maintains the detector 14 at the predetermined position and orientation with respect to the radiation source 12. As the motion controller 16 moves the radiation source 12 to a new angular position, the motion controller 16 also moves the detector 14 to a corresponding angular position. Similar to the radiation source 12, in other embodiments the detector 14 may be manually moved to different angular positions.

Figure 2:
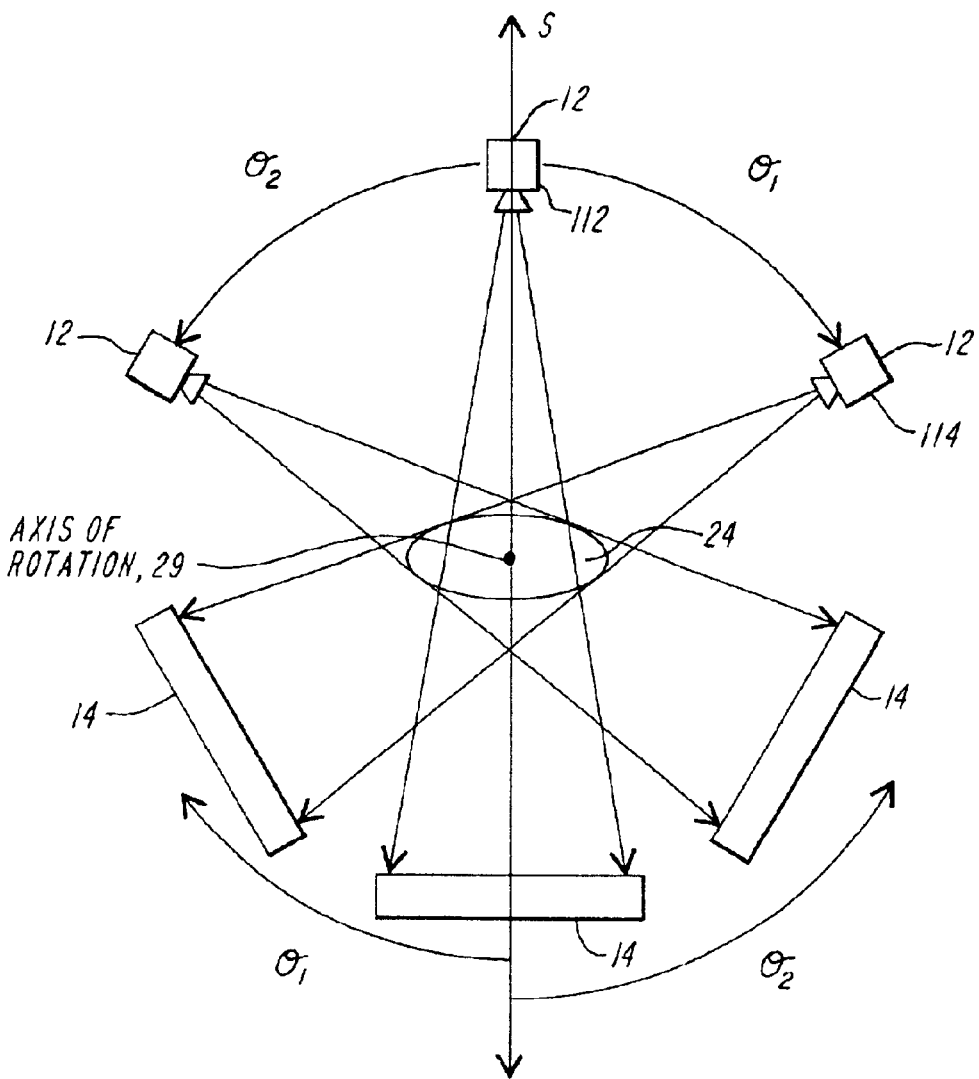
FIG. 2 is a schematic operational representation of the radiation source and detector of FIG. 1.

FIG. 2 shows an operational representation of the radiation source 12 and the detector 14 of the imaging system 10 of FIG. 1. The motion controller 16 (not shown) moves the radiation source 12 and the detector 14 to different angular positions $\theta_1$ and $\theta_2$ with respect to an axis S that extends through approximately the center of the target scene 24. In another embodiment, the axis S extends through the center of the stationary object 22. The motion controller 16 pivots the radiation source 12 and detector 14 about an axis of rotation 29, which is perpendicular to the axis S. In one embodiment, the axis of rotation 29 is located in the center of the target scene 24. In another embodiment, the axis of rotation 29 is located in the center of the object 22. At each angular position $\theta_1$ and $\theta_2$, the radiation source 12 emits radiation toward the target scene 24.

As the radiation source 12 moves to the different angular positions $\theta_1$ and $\theta_2$, the detector 14 moves to corresponding angular positions in order to receive the radiation emitted by the radiation source 12. A low noise detector suitable for use in a system of the invention is described in U.S. Pat. No. 6,448,544 entitled "Low noise, high resolution image detection system and method," herein incorporated by reference. Referring to FIG. 1, the detector 14 converts the incident radiation from the radiation source 12 into radiation transmission data 28. The radiation transmission data 28 represents the measured intensity of the radiation transmitted through the target scene 24 for each angular position of the radiation source 12. The radiation transmission data 28 is processed by the image processor 20 to create a three-dimensional image of the target scene 24 and the object 22 within the target scene 24.

In one embodiment, the resolution of the detector 14 remains fixed as it collects radiation transmitted through the object 22 for each angular position of the radiation source 12. In another embodiment, the detector 14 is a variable spatial resolution detector and is controlled by the resolution controller 18. The resolution controller 18 varies the spatial resolution of the detector 14 in response to the angular position from which the radiation is emitted by the radiation source 12 toward the target scene 24. In another embodiment, the target scene 24 is a three-dimensional scene and the resolution controller 18 controls the detector 14 to produce high resolution radiation transmission data for two dimensions of the three-dimensional scene and low resolution radiation transmission data for the third dimension of the three-dimensional scene.

In one such embodiment, the target scene 24 is defined by a rectangular coordinate system having X, Y and Z axes. In one embodiment, the detector 14 produces high resolution radiation transmission data for the X and Y directions and low resolution radiation transmission data for the Z direction, the Z direction being the vertical direction. Methods for varying the spatial resolution of the detector 14 will be described in detail below in the discussion of FIG. 10.

In some embodiments, the radiation dose to which the object is exposed varies as a function of the angular position of the radiation source. For example, the radiation dose utilized to acquire an image with the source at an angular position close to the XY plane can be higher than a dose for acquiring an image with the source nearly perpendicular to the XY plane. The change in the radiation dose can be also done in combination with varying the resolution of the detector as a function of the angular position of the source.

In one embodiment, the detector 14 is a planar detector and includes a two dimensional planar array of detector elements or pixels. The planar array of detector elements lies in a detector plane DP that is approximately perpendicular to the line L 27. In an embodiment in which the radiation source is a source of x-ray radiation, each of the pixel elements may include a scintillator element and a photodiode. The scintillator elements produce light photons in response to incident x-rays. The photodiode of a particular detector element produces a digitized signal representation of the x-ray flux incident on the corresponding scintillator element. Other types of flat or curved digital x-ray detectors may be used.

The image processor 20 interrogates each of the pixel elements to obtain digital data representative of the distribution of x-ray intensities at the different parts of the detector 14. In one embodiment, the pixel elements of the detector 14 are part of a small geometry integrated circuit array, enabling generation of a high resolution image representation. In other embodiments, charge coupled devices (CCDs) or a direct digital detector can be used. A direct digital detector directly converts x-rays to digital signals.

In one embodiment, the motion controller 16 is a computer which is programmed to control the angular position of the radiation source 12 and the detector 14. The resolution controller 18 is also preferably a computer programmed to vary the spatial resolution of the detector 14 in response to the angular position of the detector 14. Further, the image processor 20 is also preferably a computer programmed to process the data produced by the detector 14 in response to the radiation incident on the detector 14. In other embodiments, a single computer may perform the functions of the motion controller 16, the resolution controller 18 and the image processor 20. In one embodiment, the imaging system 10 also includes an exposure controller that controls the emission of radiation from the radiation source 12.

Figure 3:
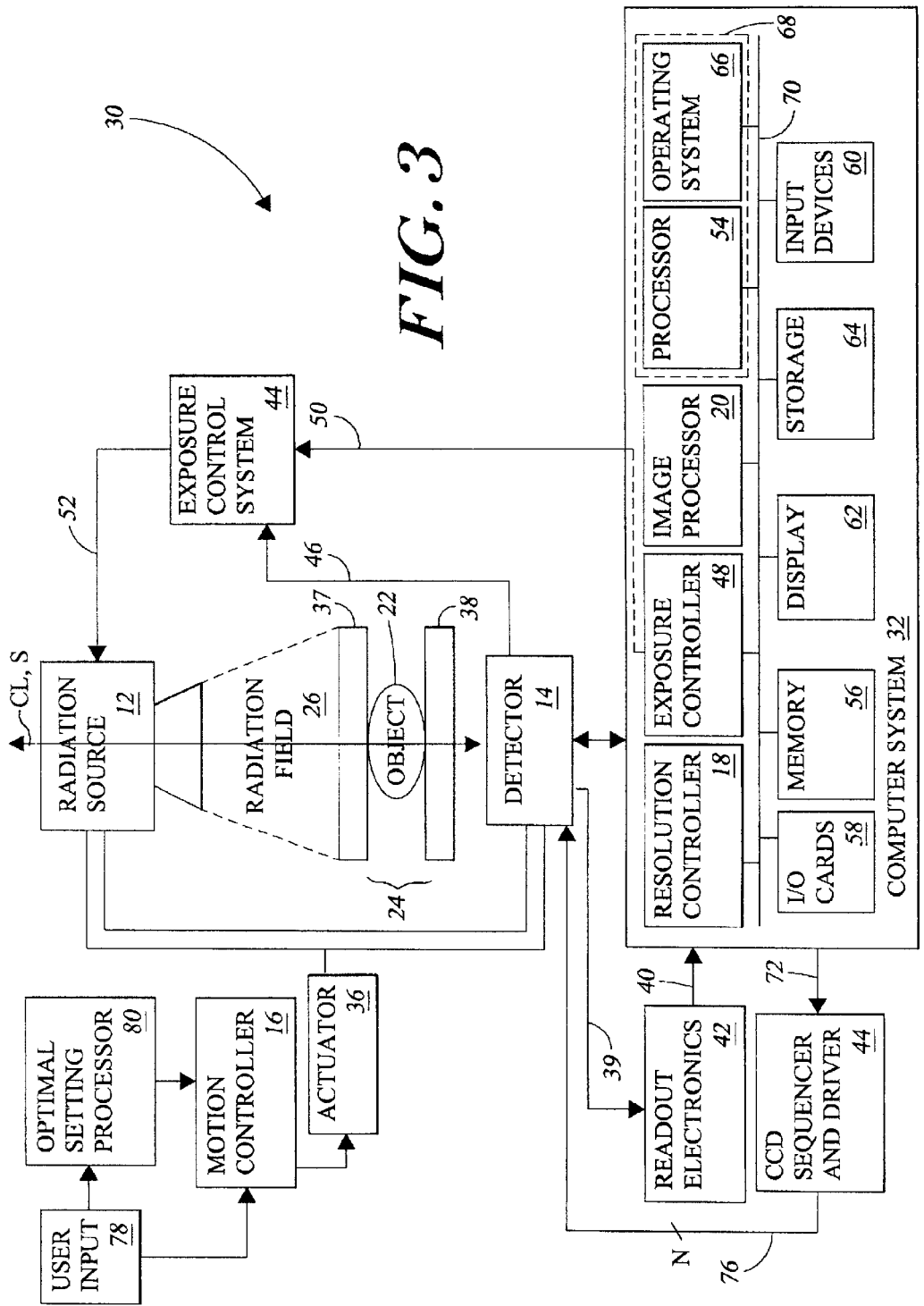
FIG. 3 is a schematic block diagram of another embodiment of an imaging system according to the invention.

FIG. 3 is a more detailed block diagram of another embodiment of an imaging system 30 according to the present invention. Similar to the imaging system 10 of FIG. 1, the imaging system 30 includes a radiation source 12, a detector 14 and a motion controller 16. In the embodiment shown in FIG. 3, the resolution controller 18 and the image processor 20 are located within a computer system 32. In other embodiments, the resolution controller 18 and the image processor 20 are independent from the computer system 32. A support structure 34 supports the radiation source 12 with respect to the detector 14 so that radiation emitted by the radiation source 12 is directed toward and received by the detector 14. In one embodiment, the support structure 34 directly mechanically couples the radiation source 12 to the detector 14. In one such embodiment, the radiation source 12 and the detector 14 are mechanically coupled so that the radiation source 12 and the detector 14 may not move independently.

The motion controller 16 sends control signals to an actuator 36 to change the angle of the radiation source 12 and the detector 14 with respect to the object 22. The object 22 is temporarily held motionless between an upper compression plate 37 and a lower compression plate 38 while the object 22 is exposed to the radiation emitted by the radiation source 12. In this embodiment, the area between the upper compression plate 37 and the lower compression plate 38 defines the target scene 24. The upper compression plate 37 and the lower compression plate 38 may be any mechanisms known in the art to keep objects substantially motionless. In another embodiment, movement of the object is compensated by the image processor 20.

In an embodiment in which the radiation source 12 is a source of x-ray radiation, the detector 14 receives the x-rays that pass through the target scene 24 and converts the incident x-rays into corresponding visible light radiation. The detector 14 includes an array of photodetectors that convert the light radiation into an electric charge that is stored. In this embodiment, the detector 14 generates analog radiation transmission data 39 representing the measured intensity of the visible light. The analog radiation transmission data 39 is received and converted into digital radiation transmission data 40 by readout electronics 42. The readout electronics 42 includes, for example, one or more analog-to-digital converters (ADCs), and communicates the digital radiation transmission data 40 to the computer system 32. The computer system 32 utilizes the digital radiation transmission data 40 to generate an image of the target scene 24.

In one embodiment, an exposure control system 44 automatically controls the exposure of the object 22 to the radiation field 26. The detector 14 provides the exposure control system 44 with an exposure intensity distribution 46 while the exposure controller 48 within the computer system 32 provides a maximum exposure value 50 to which the object 22 may be exposed. The exposure control system 44 monitors the exposure intensity distribution 46 and, when it equals or exceeds the maximum exposure value 50, generates an exposure control signal 52 that causes the radiation source 12 to cease generating the radiation field 26.

As described above, the readout electronics 42 provides the digital radiation transmission data 40 to the computer system 32. The digital radiation transmission data 40 is processed by the image processor 20 to generate digital images for subsequent display and storage. In one embodiment, the image processor 20 generates a three-dimensional image. The image processor 20 is preferably an application program executing in the computer system 32, although other implementations are possible. The computer system 32 is preferably a general purpose computer system, which is programmable using a high level computer programming language. The computer system 32 includes a processor 54, memory 56, input/output (I/O) interface cards 58, input devices 60 such as a keyboard and a pointing device and a display 62. The memory 56 is used for storage of program instructions and for storage of results of calculations performed by the processor 54. The memory 56 can include random access memory (RAM), the display 62 is preferably a high resolution CRT which is logically or physically divided into an array of picture elements commonly referred to as pixels. The input/output (I/O) interface cards 58 may be modem cards, network interface cards, sound cards, etc. The storage units 64 may include a hard disk drive, a tape storage system, CD-ROM drives, a floppy disk system and the like.

The processor 54 is typically a commercially available processor, such as the Pentium microprocessor, PowerPC microprocessor, SPARC processor, PA-RISC processor or 68000 series microprocessor. Many other processors are also available. Such a processor usually executes a program referred to as an operating system 66, such as the various versions of the Windows, NetWare, and Unix operating systems, among others. The operating system 66 controls the execution of other computer programs such as a graphical user interface (not shown) and the image processor 20, and provides scheduling, input-output control, file and data management, memory management, communication control and related services. The processor 54 and the operating system 66 define a computer platform shown by a dashed block 68, for which application programs in high level programming languages are written. The functional elements of the computer system 32 communicate with each other via a communication system such as a bus 70.

The image processor 20 controls the photodetectors in the detector 14. In one embodiment, the photodetectors are CCD detectors. In this embodiment, the computer system 32 generates CCD digital control signals 72 which are received and processed by a CCD sequencer and driver 74. The CCD sequencer and driver 74 are typically implemented in circuitry to generate CCD analog control signals 76 over N number of control lines to the detector 14. The CCD sequencer and driver 74 perform well-known functions to control CCD detector operations in response to digital control data 72, including configuration, exposure control and data read out, among others.

As described above, the motion controller 16 controls the actuator 36 to move the radiation source 12 and the detector 14 to different angular positions with respect to the axis S and the object 22. In one embodiment, the motion controller 16 receives input from a user 78 regarding the angular positions θ to which the radiation source 12 is to be moved. In another embodiment, the imaging system 30 also includes an optimal setting processor 80. The optimal setting processor 80 receives input from a user 78 regarding the dimensions of the object 22 to be imaged. Based on the dimensions of the object 22, the optimal setting processor 80 determines the angular positions θ to which the radiation source 12 is to be moved to generate a sufficient number of images. In another embodiment, the user enters the desired resolution for each acquired image. In another embodiment, the optimal setting processor 80 determines the resolution to be used for each image. In yet another embodiment, the optimal setting processor 80 uses default resolutions if the user does not select resolutions to be used.

Figure 4:
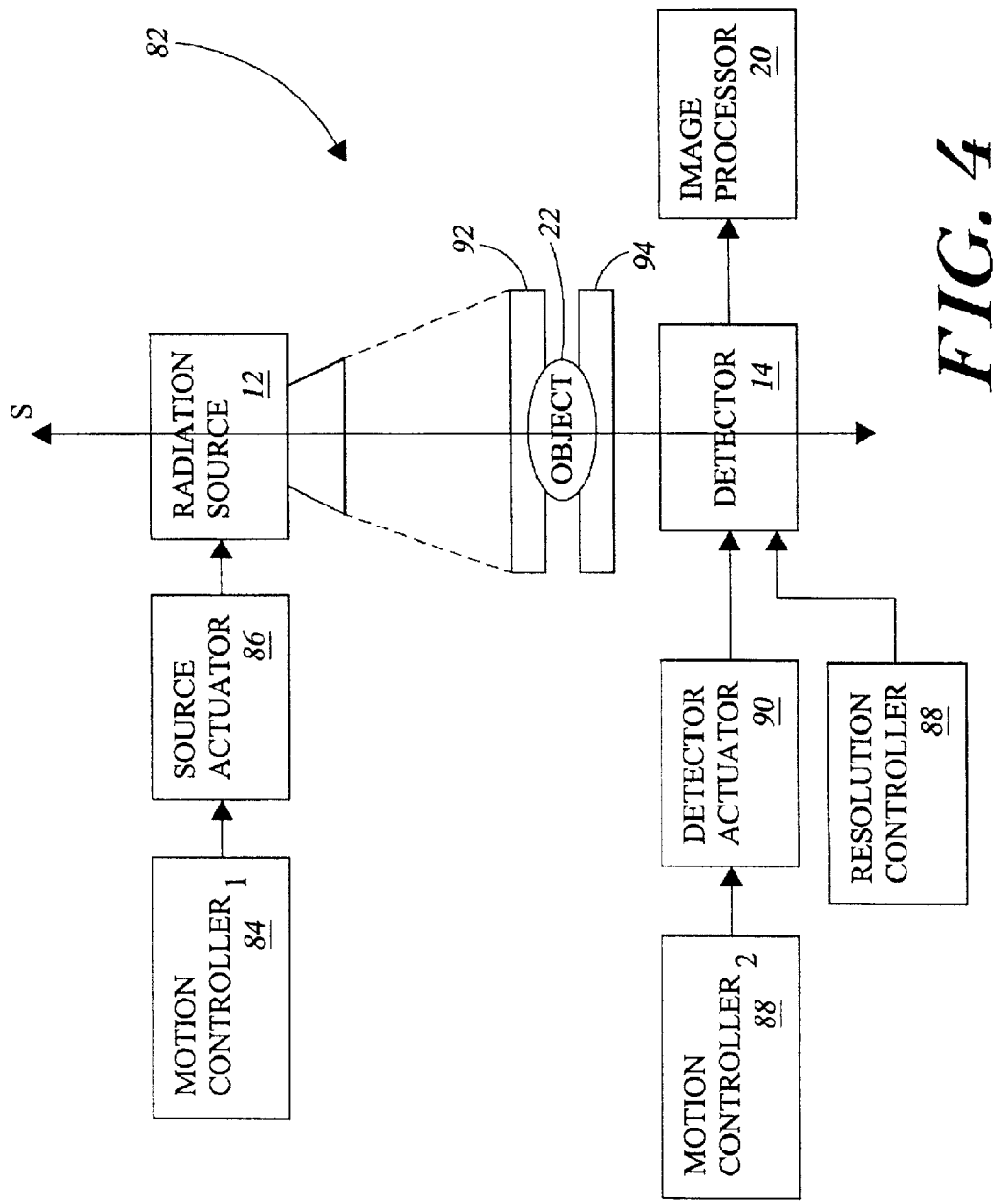
FIG. 4 is a schematic block diagram of an embodiment of an imaging system having a separate motion controller and actuator for the radiation source and the detector.

FIG. 4 shows another embodiment of an imaging system 82 according to the present invention. The imaging system 82 includes a first motion controller 84 and a source actuator 86 for moving the radiation source 12 to different angular positions. The imaging system 82 includes a separate second motion controller 88 and a detector actuator 90 for moving the detector 14 to different angular positions. The second motion controller 88 controls the detector actuator 90 to move the detector 14 in response to the angular position of the radiation source 12. The imaging system 82 also includes an upper compression plate 92 and a lower compression plate 94 which are shaped to conform to the shape of the object 22.

Figure 5:
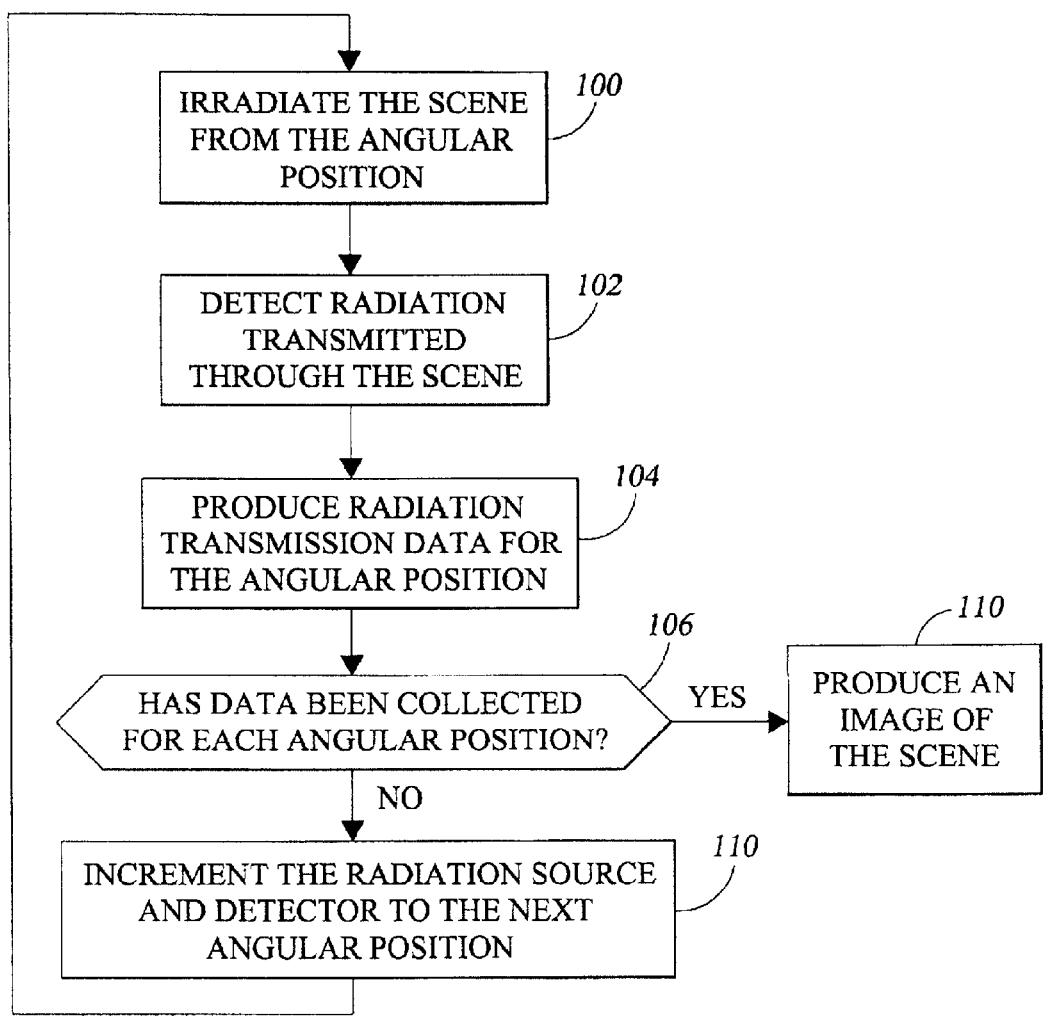
FIG. 5 is a flow chart illustrating the steps performed by an imaging system according to the present invention to generate an image of the target scene.

FIG. 5 is a flowchart illustrating the steps performed by the imaging system 10 according to the present invention for generating an image of the target scene 24. In step 100, the radiation source 12 and the detector 14 are moved to a first angular position and the radiation source 12 irradiates the target scene 24. The detector 14 detects the radiation transmitted through the scene 24 in step 102 and produces radiation transmission data 28 for the initial angular position in step 104. In step 106, the imaging system 10 determines if data has been collected for each angular position dictated by the motion controller 16. If data has been collected for each angular position, the image processor 20 produces an image of the target scene 24 in step 108. If data has not been collected for each angular position, the motion controller 16 increments the radiation source 12 and the detector 14 to the next angular position in step 110. The imaging system 10 repeats steps 100–110 until data has been collected for each angular position dictated by the motion controller 16 and an image of the scene is produced.

As illustrated by the flowchart of FIG. 5, a series of data images are collected, each at a different angular position. In one embodiment, cone-beam reconstruction methods are used with the two-dimensional detector to develop the three-dimensional image of the scene. In the embodiment shown in FIG. 3, the optimal setting processor 80 determines the number of data images to be collected and the angle for each data image.

Figure 6:
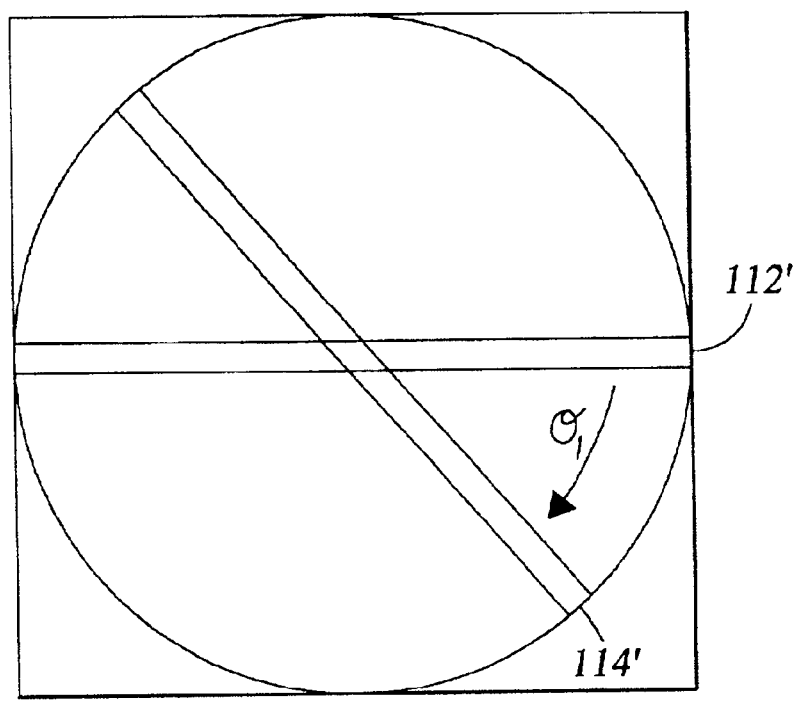
FIG. 6 is a graphical representation in the frequency domain of transmission images collected in the spatial domain.

The collection process can be better understood by referring to a frequency domain representation of the collection process. FIG. 6 shows a diagram illustrating the relationship of the object projections in the spatial domain collected by the imaging system in FIG. 2 to central slices in the frequency domain. If the distance from the radiation source 12 to the object 22 is large, as in the case of parallel illumination, the Fourier transform of a single transmission image is equal to a plane through the three-dimensional Fourier transform of the object. In one embodiment, $D_{SOURCE}$ is considered to be large if it is greater than approximately 1000 times the diameter of the object 22. The object projection collected at the central angular position 112 of the radiation source 12 in FIG. 2 corresponds to the central slice 112 of FIG. 6 and the object projection collected at the angular position 114 of the radiation source 12 after being moved through an angle $\theta_1$ corresponds to the central slice 114 of FIG. 6. If the distance from the radiation source 12 to the object 22 is small, as in the case of cone beam illumination, the above description serves as a good approximation.

In order to perform a complete three-dimensional reconstruction from a series of transmission images, a sufficient number of images must be collected to sample the entire Fourier volume at a spacing of 1/D, where D is the diameter of the object, to a radius of 1/r, where r is the desired resolution. Thus, the number of two-dimensional images N required to calculate a complete three-dimensional reconstruction is defined by the equation $N=\pi D/r$. For example, in a mammography application, to image a breast having a diameter of 10 centimeters at 0.1 millimeter resolution would require more than 3000 images. This technique is illustrated in FIG. 7A which is a representation in Fourier space of an object which is completely sampled using symmetric resolution. The total dose of radiation required for developing the three-dimensional image is a function of the number of images needed, the noise introduced by the detector and the desired signal-to-noise ratio (SNR). Therefore, reducing the number of images required reduces the total dose of radiation to which the object being imaged. A problem with reducing the number of images is degradation of three-dimensional image quality and spatial resolution.

Figure 7C:
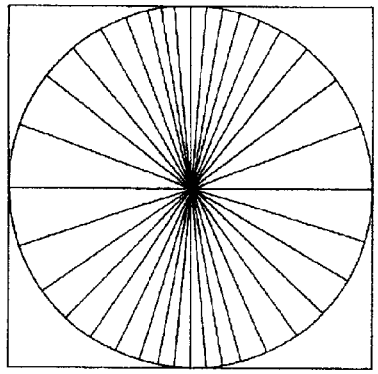
FIGS. 7A–7F are graphical representations in the frequency domain of transmission images collected in the spatial domain.
Figure 7F:
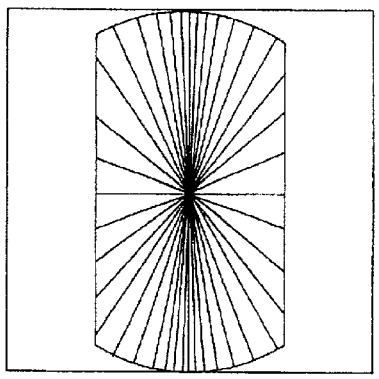
Figure 7B:
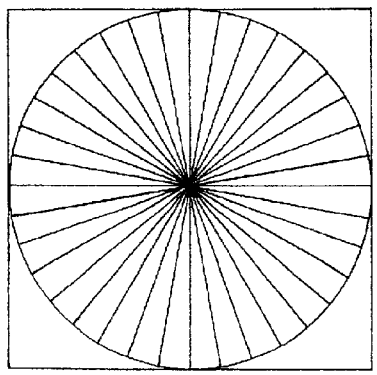

FIGS. 7B–7F illustrate possible image collection techniques according to the invention for reducing the number of images while retaining the ability to generate three-dimensional images. Each of these techniques collects either fewer images, images at lower spatial resolution, or both. In one embodiment, advanced fitting algorithms and constraints are used to improve image quality. The fitting algorithms include, but are not limited to, maximum likelihood, maximum entropy and conjugate gradients. The constraints include intensity constraints, such as the minimum and maximum tissue absorption and the distribution of tissue, and spatial constraints, such as the boundary of the object. FIG. 7B is a representation in Fourier space of an object using half the number of images as in FIG. 7A. In this case, the resolution of the reconstruction is only half of the resolution that could be obtained with the full number of images. In the representation of FIG. 7B, the added constraints and fitting methods minimize the effects of the lower resolution data. FIG. 7C is a representation in Fourier space of an object which has been sampled using non-uniform angular spacing. That is, the angle between each angular position used to collect an image is varied. In this embodiment, better resolution is obtained in one orientation than the other orientation. The resulting 3D reconstruction has high spatial resolution in horizontal planes with lower vertical spatial resolution. In one embodiment, the data can be viewed as a series of thin planes through the object. For example, in one such embodiment, each plane in the series of planes is approximately 1 millimeter thick.

Figure 7E:
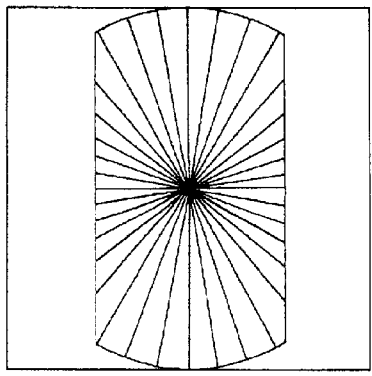
Figure 7A:
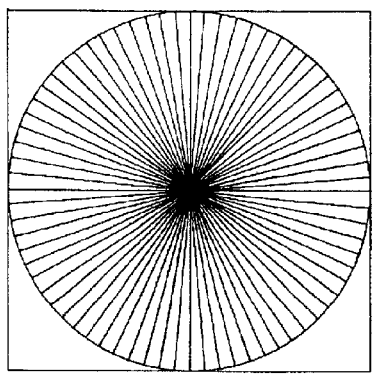
Figure 7D:
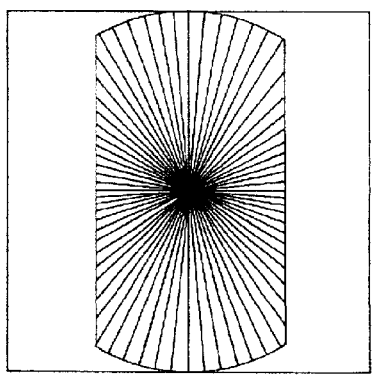

FIGS. 7D–7F are representations in Fourier space of an object which has been sampled using non-uniform spatial resolution. In certain embodiments, utilizing non-uniform spatial resolution results in a further reduction in the dose applied to the object 22. In FIG. 7D, the spatial resolution of each image is chosen such that the image data forms a thick slice through the frequency domain. In the illustrated example, the vertical images are collected at approximately one-half the resolution of the horizontal images. In another embodiment, using a ratio of 1/20 generates a three-dimensional map with 1 mm resolution in the vertical direction and 0.05 mm resolution in the horizontal direction. As described above, this data set can then be viewed as a series of thin (1 mm thick) imaging planes through the object. This method requires 1/10 of the dose and approximately ½ the number of images as required by the example of FIG. 7A, with an approximate 20 fold reduction in imaging time.

Decreasing the thickness of the imaging planes allows for a further reduction of these requirements. FIG. 7E is a representation in Fourier space of an object utilizing half the number of images as in FIG. 7D. FIG. 7F is a representation in Fourier space of an object which has been sampled using non-uniform angular spacing and non-uniform spatial resolution. To perform a three-dimensional reconstruction, the representations in FIGS. 7E and 7F are also generated using constraints and advanced fitting methods.

Figure 8A:
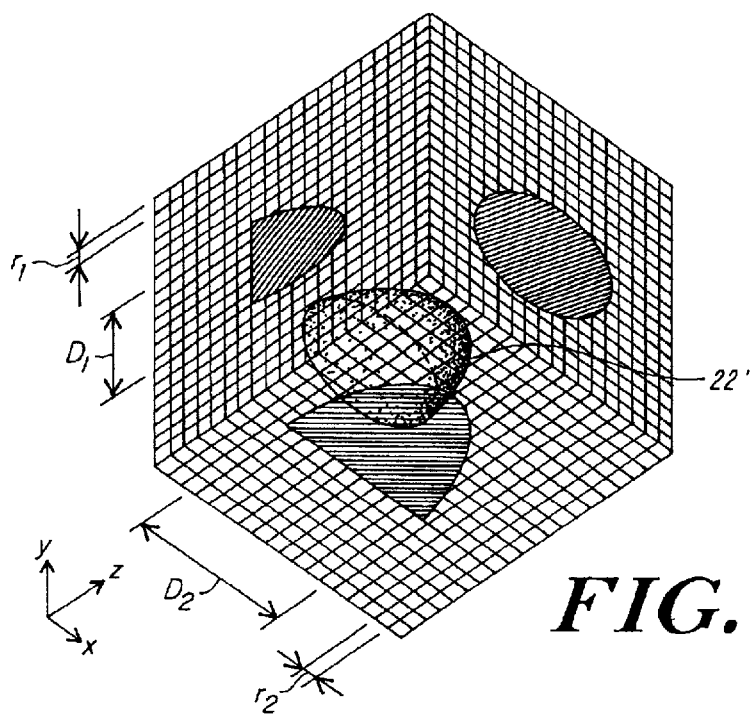
FIG. 8A is a graphical representation of an object in the spatial domain.
Figure 8B:
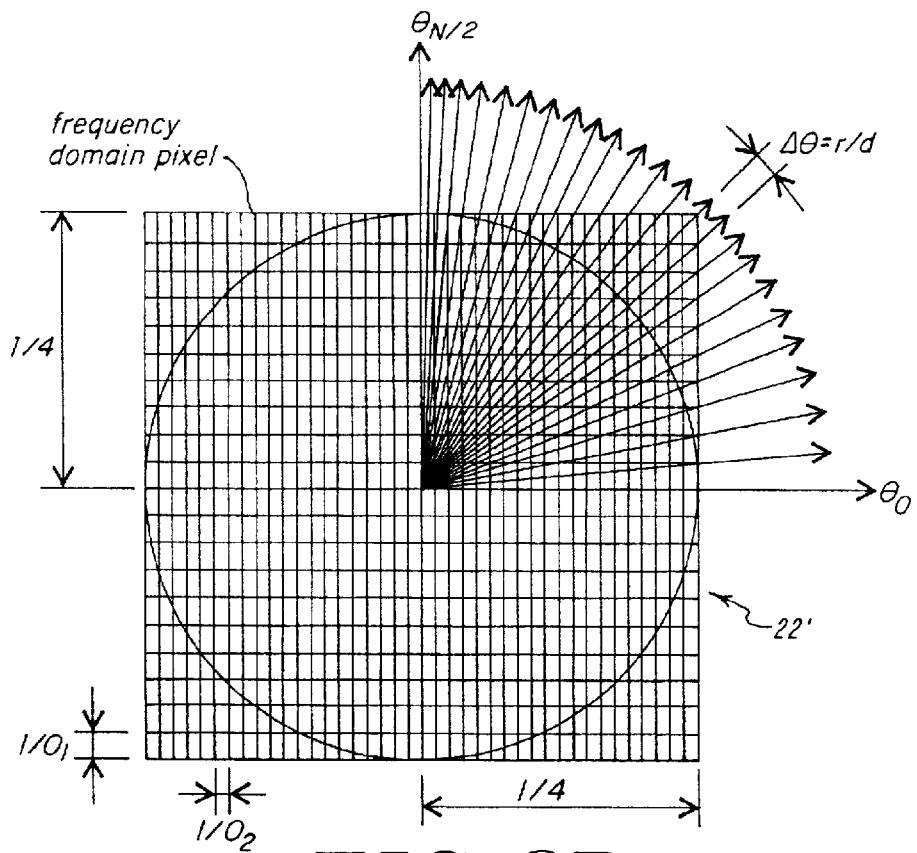
FIG. 8B is a graphical representation of the object in FIG. 8A in the frequency domain.

FIG. 8A is a graphical representation of the object 22 in the spatial domain. FIG. 8B is a graphical representation of the object 22 from FIG. 7A in the frequency domain. Objects, such as object 22, which have unequal dimensions in the reconstruction (x,y) plane are particularly well suited for an image acquisition geometry using non-uniform angular spacing and non-uniform spatial resolution. Because $D_1$ is not equal to $D_2$, the lattice in Fourier space is not the same in X and Y directions. To sample all lattice points, one collection strategy is to use non-uniform angular spacing as shown in FIG. 8B. In FIG. 8B, the change in the angle $\theta$ decreases as the angular position moves from $\theta_0$ to $\theta_{N/2}$. Another collection strategy is to vary the spatial resolution as the angular position changes. For example, in one embodiment, the imaging system allows the resolution in the Y-direction to be less than the resolution in the X-direction. Allowing the resolution to vary enables fewer images to be required.

Figure 9:
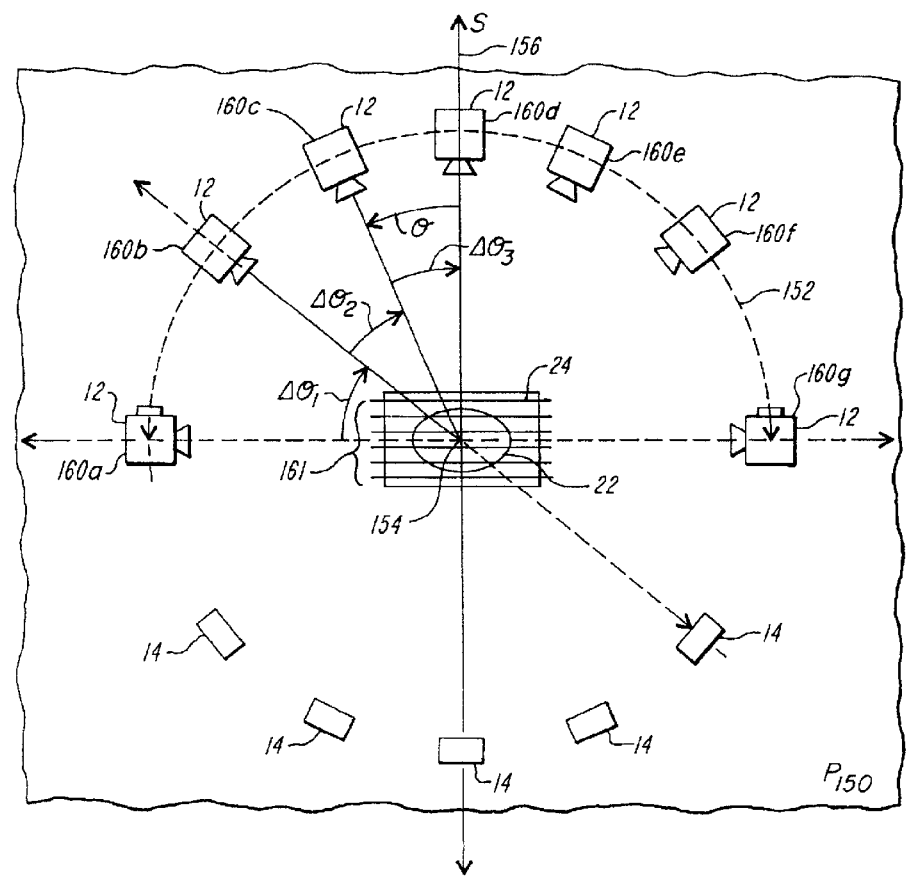
FIG. 9 is a schematic operational representation of the system of FIG. 1 using an embodiment of the image acquisition geometry according to the invention.

FIG. 9 shows an operational representation of the system 10 of FIG. 1 using the non-uniform angular spacing technique described above to control the irradiation of the target scene 24 and the object 22 by the radiation source 12. The radiation source 12 is capable of emitting radiation toward the target scene 24 and the object 22 from a plurality of angular positions θ. The plurality of angular positions θ are located in a plane P 150 which extends through the radiation source 12 and the target scene 24. In one embodiment, the plane P 150 extends through approximately the center of the radiation source 12 and approximately the center of the target scene 24. In another embodiment, the plurality of angular positions θ, to which the radiation source 12 may be moved, define an arc 152 about the target scene 24. The arc 152 spans the plane P 150 formed by the axes X and Z and has an axis of rotation 154 along a line S 156 in the plane P that is perpendicular to the target scene 24 and that extends through the target scene 24. In one embodiment, the plane P 150 extends through approximately the center of the target scene 24. The angle θ is given by the angle of the direction of the radiation source 12 relative to the line S 156.

FIG. 9 illustrates the acquisition of images from discrete source positions 160a–g along the arc 152 above the object 22. For clarity of illustration, only seven radiation source positions are shown. In other embodiments, the radiation source 12 can be moved to any number of radiation source positions 160. As the source 12 moves from angular position 160a to angular position 160b, the source moves through an angle $\Delta\theta_1$. Similarly, as the source 12 moves from angular position 160b to angular position 160c, the source moves through an angle $\Delta\theta_2$. To vary the angular spacing, the angle $\Delta\theta_1$ is different than the angle $\Delta\theta_2$. Similarly, the angle $\Delta\theta_3$ is different from the angles $\Delta\theta_1$ and $\Delta\theta_2$. In one embodiment, the angle Δθ decreases as the radiation source 12 transitions from angular position 160a through angular positions 160b and 160c to angular position 160d and then increases as the radiation source 12 transitions from angular position 160d through angular positions 160e and 160f to angular position 160g. That is, $\Delta\theta_1$ is greater than $\Delta\theta_2$, which is greater than $\Delta\theta_3$. This image acquisition geometry decreases the total number of images required.

In another embodiment, the target scene 24 may be defined by a plurality of horizontal planes 161. In one such embodiment, the angular spacing of the steps along the arc 152 decreases as the source 12 moves from a first angular position 160a, which is substantially parallel to the plurality of horizontal planes 161, through angular positions 160b and 160c to the angular position 160d, which is substantially perpendicular to the plurality of horizontal planes 161.

The images are acquired at each angle θ by the detector 14. The radiation dose emitted by the radiation source 12 at each angle θ is low, with the total radiation dose for all images being comparable to the dose used for a standard mammogram. A standard mammogram typically requires approximately 80 mrad per image for an average size breast. Once the images are collected at each angular position, a three-dimensional image of the object is generated. The increase in the number of images collected compared to the two images collected in conventional x-ray mammography increases the ability to discern structures at different levels. In one embodiment, the resulting three-dimensional image has a resolution in two orientations equal to the full detector resolution and a lower resolution in the third orientation. For example, in an embodiment in which the full detector resolution is 50 microns, the resolution in the third orientation may be approximately 2–10 mm. The three-dimensional reconstruction can be viewed as a series of layers, also referred to as planar projections, each at the full detector resolution. The image of overlapping tissue structures that would be seen in a conventional mammogram is laterally separated into different planar projections. Each planar projection may be analyzed for abnormal structures.

FIG. 10 shows an embodiment of a photodetector array 170 according to the invention, which is an 8×8 array of photodetectors and includes 64 individual photodetectors 172 arranged in a square pattern having eight columns 174 and eight rows 176. In other embodiments, the photodetector array 170 may have any desired number of photodetectors. In yet other embodiments, the individual photodetectors 172 in the array 170 may be arranged in a rectangular pattern, a circular pattern or any other desired pattern.

Each time one of the photodetectors 172 or pixels is read by the read out electronics a certain amount of error is introduced. One method for reducing the resolution of the photodetector array 172, is to read out two pixels $P_1$ and $P_2$ individually and then average the values. This process is then repeated for the next two pixels $P_3$ and $P_4$ until all of the pixels are read. By averaging the values of sets of two pixels, the resolution of the detector is reduced by ½. Other quantities of pixels may be averaged to attain different resolutions. If each pixel has a read noise of $\sigma_R$, the error introduced is equal to $(N)^{1/2} \sigma_R$ where N is the number of pixels averaged.

Another method for changing the resolution is to combine the pixels before the pixels are read by the readout electronics 42. For example, if photodetector array 170 is a CCD array, $P_1$ and $P_2$ could be combined and then the combined value read by the readout electronics 42.

As described above, the resolution controller 18 controls the resolution of the detector 14. To achieve non-uniform spatial resolution, the resolution controller 18 varies the resolution of the detector 14 in response to the angular position θ of the radiation source. Referring again to FIG. 9, in one embodiment the resolution controller 18 changes the spatial resolution of the detector as the radiation source 12 moves from angular position 160a to angular position 160b. In another embodiment, the resolution controller 18 increases the spatial resolution of the detector 14 as the radiation source transitions from angular position 160a to angular position 160d and decreases the spatial resolution of the detector 14 as the radiation source transitions from angular position 160d to angular position 160g. In this embodiment, the spatial resolution in the horizontal direction is less than the spatial resolution in the vertical direction. For this method, the read noise for each value is only $\sigma_R$.

As described above, the image processor 20 generates a three-dimensional image of the object 22 in the target scene 24. In one embodiment, the image processor 20 is implemented in software. The software routines for performing the image processing methodology in accordance with aspects of the present invention typically reside in memory 56 and/or disk storage devices 64, and may be stored on a computer-readable medium such as magnetic disk, compact disc or magnetic tape and may be loaded into the computer system 32 using an appropriate peripheral device as known in the art.

The image processor 20 may be implemented in any well-known programming language such as C or C++. Those skilled in the art will appreciate that different implementations, including different function names, programming languages, data structures, and/or algorithms other than those described herein may also be used in embodiments of the present invention. It should be further understood that the present invention is not limited to a particular computer platform, particular operating system, particular processor, or a particular high level programming language, and that the hardware components identified above are given by way of example only. The image processor 20 may be implemented, for example, in dedicated hardware, firmware, or any combination of hardware, firmware and software.

As described above, the image processor 20 processes the digital image data 40 to generate a digital image suitable for use by the computer system 32. The data collection technique described above is particularly useful in imaging breasts using a full-field digital mammography system. The radiation dose is low and comparable to conventional mammography systems. The collection geometry described above will improve early breast cancer detection, especially for women with radiographically dense breasts.

Image reconstruction techniques for developing the three-dimensional image include, for example, simple back projection, filtered back projection and computed planar mammography (CPM) techniques. The CPM techniques include non-linear iterative fitting methods. CPM uses projections collected on the two-dimensional detector 14 to reconstruct the three-dimensional volume of the object. The imaging geometry uses reconstruction methods known as cone-beam reconstructions. A cone-beam reconstruction uses a conical-shape x-ray beam to image the object. After the images have been collected using the image acquisition geometry described above, the CPM methodology uses advanced fitting algorithms and constraints.

As described above, one of the problems with conventional mammography systems is structure noise. Structure noise is caused by overlapping structures in the object obscuring clear visualization of the object. Other sources of noise include uncertainties due to photon statistics, scattered radiation and noise sources intrinsic to the detection system. In an electronic detector, the noise sources include non-uniformity distortions, spatial distortions, readout noise and dark noise. One method for increasing the sensitivity of the system is to decrease the uncertainty in the signal by increasing the dose. Another method for increasing the sensitivity of the system is to reduce detector noise by utilizing a more sensitive detector.

In one embodiment, the detector 14 is a low-noise digital detector. Using a low-noise detector has the effect of lowering the total dose of radiation applied to the object 22. The disadvantage of taking N low-dose images rather than a single integrated image is the increase in read noise. For a detection system having high read noise, such as screen-film, high doses of radiation are required in order to achieve an acceptable SNR as the number of images increases. Using a low-noise detector enables a larger number of images to be collected with the same total dose as a single exposure without significantly degrading the SNR. Using the low-noise detector described in U.S. Pat. No. 6,448,544, a single exposure of 2000 x-ray photons/pixel generates a SNR of approximately 31. Collecting 10 images using the same total dose decreases the SNR to approximately 30, and collecting 100 images with the same total dose decreases the SNR to approximately 22. Therefore, utilizing very low noise digital detectors allows collection of multiple projections for CT reconstruction without incurring a large noise penalty.

One embodiment of a low-noise detector is shown in FIGS. 11A and 11B. In this embodiment, the radiation source 12 is a source of x-ray radiation. The detector includes an x-ray-to-light converter, six fiber optic image couplers, and six CCD image sensors 202. The x-ray source 12 (not shown) irradiates an object 22 (also not shown). The radiation passing through the object 22 is converted by a scintillation plate or phosphor x-ray-to-light converter that coverts x-ray radiation into light photons. Individual light photons pass through one of an array of fiberoptic tapers 200 and are sensed by a CCD detector 202, fixedly secured to an output surface of each of the fiberoptic tapers 200. A socket provides electrical connectivity to other components of the detector 14. To reduce noise and provide the improved dynamic range and spatial resolution for early cancer detection, each CCD detector 202 is thermally coupled and cooled by a cooling module 204. A cooling manifold 206 provides the necessary heat transfer to properly cool a thermoelectric cooling device of cooling module 204. The fiberoptic taper 200 is structurally supported by a flange 208. Each flange 208 is connected to a mounting frame 210 via four concentric alignment screw pairs 212.

The position and orientation of each flange 208 is adjusted with concentric screw pairs 212. Flanges 208, mounting frame 210, manifold 206 and cooling module 204 structurally inter-operate to form an air-tight enclosure that is preferably maintained with minimal moisture to create an optimal operational environment for CCD detector 202. The components of the detector 14 are contained within a light-tight box.

FIG. 11A is an exploded view of a sensor module 214, a plurality of which comprise a sensor array 218. FIG. 11B is an exploded perspective view of an exemplary arrangement of six such sensor modules 214 as they would be arranged when installed in a sensor array 218. The mounting frame 216 removably secures a plurality of sensor modules 214 in a fixed relative arrangement.

The sensor array 218 provides a modular arrangement of a minimal number of sensor modules 214 each having a high demagnification fiberoptic taper 200 coupled to a photodetector array such as CCD detector 202. The sensor modules 214 are optimally arranged in sensor array 218 so as to substantially minimize data loss typically associated with the implementation of a mosaic of fiberoptic tapers. Sensor modules 214 are removably secured within sensor array 218 to facilitate individual removal for repair and maintenance. In addition, when installed in sensor array 218, sensor modules 214 are individually suspended in a non-contact arrangement to minimize damage due to shock, vibration and thermal expansion. Thus, sensor array 218 advantageously provides a high resolution detector 14 that substantially eliminates the mechanical complexity typically associated with image sensors having an array of fiberoptic tapers. The sensor array 218 can be repaired and maintained quickly and inexpensively, and substantially withstands damage due to shocks and vibration experienced with normal use in the anticipated environment.

FIG. 11A is an exploded view of one embodiment of sensor module 214. Sensor module 214 primarily includes three components: a CCD detector 202, a flange 208 and a fiberoptic taper 200. The CCD detector 202 is rigidly attached and optically coupled to output surface 220 of fiberoptic taper 200 to receive light transferred through fiberoptic taper 200 from input surface 222. The sensor modules 214 are constructed and arranged to minimize damage or performance degradation due to shock and vibration. To this end, CCD detector 202 is rigidly attached to fiberoptic taper 200 such that movement of fiberoptic taper 200 will not interfere with the operation of CCD detector

202. Preferably, an optical epoxy is used to attach CCD detector 202 to fiberoptic taper 200.

Preferably, an optical epoxy, such as the optical epoxy TRA-CON F114 available from TraCon, Inc, Bedford, Mass., USA, is utilized to attach CCD detector 202 to fiberoptic taper 200. Other types of optical epoxy may also be employed. It should be appreciated by those of ordinary skill in the art that the disclosed embodiment of CCD detector 202 is illustrative only and that other photodetectors may be used. For example, in alternative embodiments, CID or CMOS photo detectors are utilized. In a preferred embodiment, however, CCD detector 202 is a THX7899 CCD available from Thomson CSF, Saint-Egreve, France, available through Thomson Components and Tubes Corp., Totana, N.J., USA.

Flange 208 structurally interconnects fiberoptic taper 200 (and CCD detector 202) to mounting frame 210. The use of flange 208 enables sensor modules 214 to be individually mounted on mounting frame 210, providing the benefits associated with a modular design such as functional compactness and individual replacement and adjustment. In addition, flange 208, when installed, provides a supporting reference platform through which the position and orientation of fiberoptic taper 200 is adjusted. Flange 208 is attached to and mechanically supports fiberoptic taper 200. Flange 208 is constructed from a material that has sufficient strength and rigidity to prevent motion of optical surface 222 when fiberoptic taper 200 is installed in mounting frame 210. For example, in one preferred embodiment, flange 208 is comprised of aluminum or aluminum alloy. Alternatively, other metals or sufficiently rigid plastics or composite materials may be used, depending upon the mass of fiberoptic taper 200 and the intended environment in which sensor array 218 is to be implemented. Selection of such materials and structure is considered to be apparent to those of ordinary skill in the relevant art.

Flange 208 is attached to fiberoptic taper 200 using a flexible adhesive to dampen the transfer of thermally-induced stresses, mechanical vibrations and shocks between flange 208 and fiberoptic taper 200. In one embodiment, a commercially available silicon adhesive such as Dow Corning 732 or General Electric Silicone II is used. Such an attachment method minimizes transmission of external forces to fiberoptic taper 200 with minimal adverse effects to the optical integrity of fiberoptic taper 200

Each flange 208 also includes a plurality of threaded bores 212 to be used for attaching flange 208 to mounting frame 216. The cross-sectional area of flange 208 is smaller than the surface area of input surface 222. As such, flanges 208 may have any shape appropriate for mounting and which provides a surface sufficient to structurally support fiberoptic tapers 200. In the illustrative embodiment, flange 208 approximates a square. In this embodiment, four bores, one in each corner of flange 208, are provided to attach flange 208 to mounting frame 216, as well as to adjust the position and orientation of flange 208 relative to mounting frame 216. Concentric adjustment screw pairs disposed in bores 212 are used in certain aspects of the invention to align fiberoptic tapers 200 so that input surfaces 222 of the array of fiberoptic tapers 200 form a substantially flat optical surface.

FIG. 11B illustrates six sensor modules 214 arranged as they would be arranged for mounting into mounting frame 216. Mounting frame 216 includes a series of passageways 224 corresponding to the number of sensor modules 214 to be included in sensor array 218. Passageways 224 are sized and dimensioned to allow CCD detector 202 and a portion of fiberoptic taper 200 to extend therethrough. In one embodiment, a gap having a size less than that of a single pixel is provided between each sensor module 214. The sensor modules 214 are attached to the mounting frame 216 by concentric leveling/mounting screws. The cooling manifold 206 is cooled by water following the path illustrated by the dashed line 226. Six cooling modules 204 are shown above the cooling manifold 206. In another embodiment, the water can follow other paths.

In one embodiment, the detector of FIGS. 11A and 11B has an imaging area of approximately 19 by 28 centimeters, an image matrix size of approximately 4000 by 6000 pixels, a pixel size of 45 micrometers, an image readout time of six seconds and a readout noise equal to the signal from two x-ray photons. The six modules comprising the detector array 218 are joined such that the space between the modules is less than one pixel, thus effectively providing a continuous image across the entire detector area.

Other low noise detectors known in the art may also be used. Preferably the detector has a low dark current and low read noise compared to the signal level and on-chip binning. The low read noise allows collection of multiple low-dose images. The low dark current and the on-chip binning allow the detector to be operated in a low spatial resolution mode without any significant penalty from added noise or readout time. As described above, CCD binning allows multiple pixels to be binned on the CCD prior to readout. In one embodiment, the low noise detector produces noise less than or equal to approximately the signal from 10 x-ray photons. In yet another embodiment, the low noise detector preferably produces noise less than or equal to approximately the signal from 4 x-ray photons. In still another embodiment, the low noise detector more preferably produces noise less than or equal to approximately the signal from 2 x-ray photons. In another embodiment, the low noise detector even more preferably produces noise less than or equal to approximately the signal from 1 x-ray photon.

Figure 12:
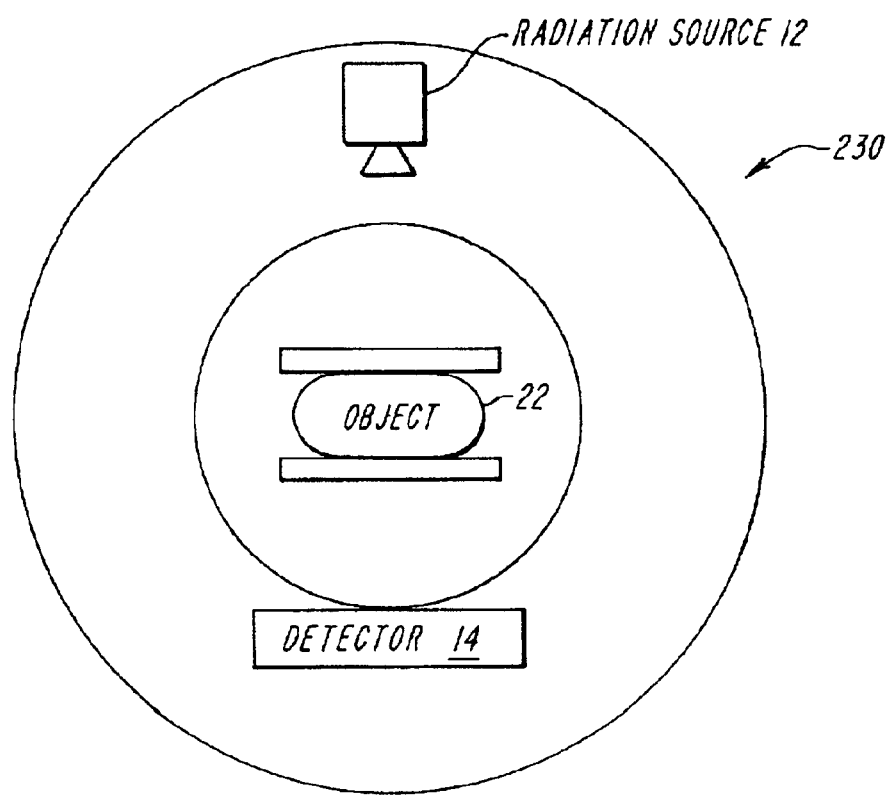
FIG. 12 is a schematic block diagram of another embodiment of an imaging system according to the invention.

FIG. 12 is a block diagram of an embodiment of an imaging system 230 in which the radiation source 12 and the detector 14 are rotated about the object 22 in a manner similar to systems used for computer tomography scans.

In other embodiments, image processing techniques are used to process the image generated by the image processor 20 to create an improved image. These image processing techniques include, for example, maximum likelihood and maximum entropy techniques.

Figure 13A:
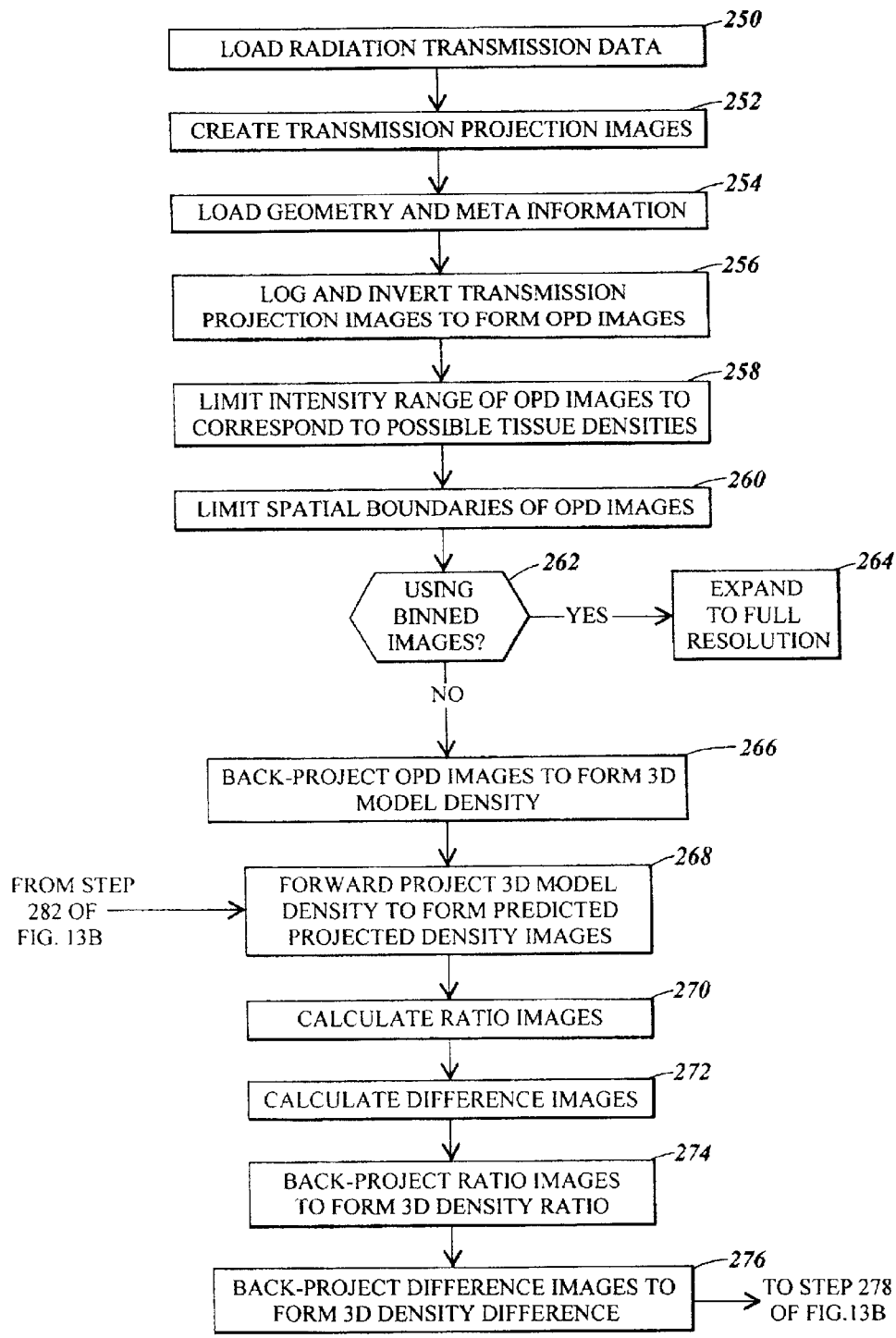
FIGS. 13A and 13B are flow charts illustrating the steps performed by an embodiment of an imaging system according to the present invention to create an improved image.
Figure 13B:
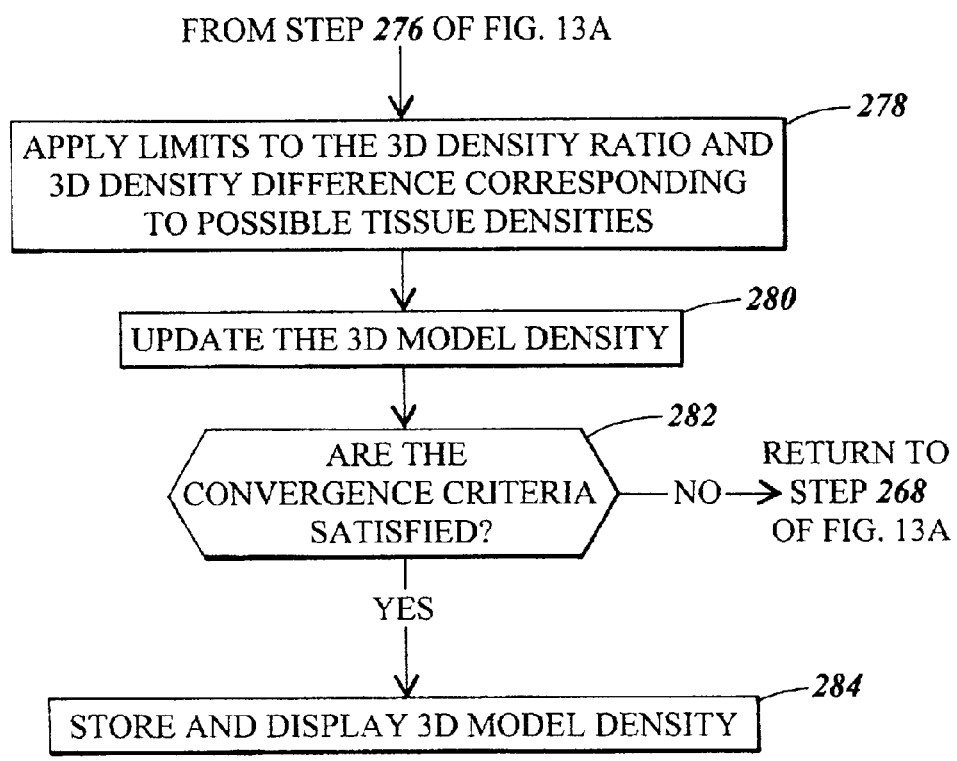

FIGS. 13A and 13B show a flow chart illustrating the steps performed by an embodiment imaging system according to the present invention to create an improved image. In step 250, the image processor 20 loads the collected radiation transmission data. Subsequently, in step 252, the image processor 20 creates transmission projection (TP) images from the radiation transmission data. The TP images represent images of the scene collected from each of the respective angular positions. The image processor 20 also loads geometry and meta information in step 254. The geometry and meta information may include the size of the detector, the size of each pixel in the detector, the geometry of the source, the angular range and spacing of the source relative to the object, and any information regarding binning that was done by the detector.

In a three-dimensional object, any volume element, or voxel, reduces the number of x-ray photons transmitted through the element by a constant fraction. Many such elements along a path through the object combine multiplicatively. Therefore, in one embodiment, in order to obtain density measurements from counting data, the log of the counting data is taken. After loading the TP images and the geometry and meta information, the image processor 20 logs and inverts the TP images to form observed projected density (OPD) images in step 256. In step 258, the image processor limits the intensity range of the OPD images to correspond to possible densities of the object being imaged. In an embodiment in which the object 22 is a part of a human body, the intensity range of the images is limited to possible tissue densities. Next, in step 260, the image processor limits the spatial boundaries of the OPD images.

In step 262, the image processor 20 determines if it is processing binned images. If the image processor 20 is processing binned images, the image processor proceeds to step 264 and expands the image to the full spatial resolution that would have been obtained had the detector not been operated in a binned mode. This operation can be performed using linear interpolation, or using other interpolating methods well known to those skilled in the art. If the image processor 20 is not using binned images, the image processor 20 proceeds directly to step 266 and back-projects the OPD images to form a three-dimensional (3D) model density. Next, in step 268, the image processor 20 forward-projects the 3D model density to form predicted projected density (PPD) images. Such forward-projection can be accomplished by utilizing, for example, the techniques described in "Image Reconstructions from Projections, The Fundamentals of Computerized Tomography" by G. T. Herman, Academic Press, New York, 1980 (e.g., chapter 6). This publication is herein referred to as "The Fundamentals of Computerized Tomography", and is herein incorporated by reference. The image processor 20 compares the OPD images with the PPD images. To perform the comparison, the image processor 20 calculates ratio (R) images according to the equation R=OPD/PPD in step 270 and calculates difference (DIFF) images according to the equation DIFF= OPD−PPD in step 272.

After comparing the OPD images to the PPD images, the image processor 20 back-projects the R images to form a 3D density ratio in step 274 and back-projects the DIFF images to form a 3D density difference in step 276. Such back-projection can be done by employing, for example, the techniques described in "The Fundamentals of Computerized Tomography" (e.g., chapter 7). In step 278, the image processor 20 applies limits to the 3D density ratio and the 3D density difference corresponding to possible densities of the object. The image processor 20 then updates the 3D model density as a function of the current 3D model density, the 3D density ratio and the 3D density difference in step 280. Methods for updating the 3D model density as a function of the current 3D model density, the 3D density ratio and the 3D density difference are well known to those skilled in the art of 3D reconstructions. The methods include summation, multiplication, and other functions, such as maximum-likelihood, maximum entropy and conjugate gradients. In the summation method, the new 3D model density is calculated by adding the current 3D model density to the 3D density difference. In the multiplication method, the new 3D model density is calculated by multiplying the current 3D model density by the 3D density ratio. The techniques described, for example, in "The Fundamentals of Computerized Tomography" (e.g., chapter 11) or in the article entitled "Multiscale Bayesian Methods for Discrete Tomography" by T. Frese, C. A. Bourman and K. Sauer, in "Discrete Tomography: Foundations, Algorithms, and Applications" pages 237–261, Birkhauser Boston, Cambridge, Mass. 1999, edited by G. T. Herman and A. Kuba can be utilized to perform 3D model density update. All of these publications are herein incorporated by reference.

The image processor 20 then determines if the convergence criteria are satisfied in step 282. If the convergence criteria are not satisfied, the image processor 20 returns to step 268. If the convergence criteria are satisfied, the image processor 20 stores and displays the 3D model density in step 284. Convergence criteria are well known to those skilled in the art of 3D reconstructions. For example, if the summation method described above is used, convergence is achieved when the 3D density difference becomes small relative to the 3D model density. In other embodiments, convergence may be judged by visual inspection of the 3D model density.

While various embodiments of the present invention have been described above, it should be understood that they have been presented by way of example only, and not limitation. Thus, the breadth and the scope of the present invention are not limited by any of the above exemplary embodiments, but are defined only in accordance with the following claims and their equivalents.

What is claimed is:

1. A method for imaging a scene, comprising the steps of irradiating a scene from a plurality of angular positions,
   detecting radiation transmitted through the scene at a plurality of different spatial resolutions corresponding to the plurality of angular positions;
   producing two-dimensional transmission data representative of the intensity of the radiation transmitted through the scene at each of the plurality of angular positions; and
   producing a three-dimensional image of the scene based on said two-dimensional transmission data.

2. The method of claim 1, wherein the step of irradiating the scene further comprises the step of irradiating the scene using x-ray radiation.

3. The method of claim 2, wherein the step of irradiating the scene further comprises the step of irradiating the scene using a total radiation dose which is less than or approximately equal to a dose of a standard screening mammogram.

4. The method of claim 3, wherein said standard dose is approximately 80 mrad per image.

5. The method of claim 1, wherein the plurality of angular positions forms an arc about the scene.

6. The method of claim 5, wherein the arc spans a plane and has an axis of rotation on a line in the plane that is perpendicular to the scene and that extends through approximately the center of the scene.

7. The method of claim 1, wherein the step of irradiating the scene further comprises the step of varying the angular spacing between the plurality of angular positions.

8. The method of claim 1, wherein the scene is a three-dimensional scene and wherein the step of producing radiation transmission data further comprises the steps of:
   producing high resolution radiation transmission data for two dimensions of the scene; and
   producing low resolution radiation transmission data for a third dimension of the scene.

9. A method of imaging an object, comprising the steps of:
   irradiating the object from a plurality of non-uniformly distributed angular positions;
   detecting radiation transmitted through the object for each of said angular positions to create two-dimensional transmission data; and constructing a three-dimensional image of the object by analyzing said radiation transmission data;

wherein the step of irradiating includes irradiating the object with a first radiation dose at one angular position of the source and irradiating the object with a second radiation dose at another angular position, said second radiation dose being different from said first radiation dose.

10. A method of imaging an object, comprising the steps of:

irradiating the object from a plurality of non-uniformly distributed angular positions, detecting radiation transmitted through the object for each of said angular positions to create two-dimensional transmission data; and constructing a three-dimensional image of the object by analyzing said radiation transmission data;

wherein the step of irradiating the object comprises selecting a sufficiently low dose of radiation for each angular irradiation such that a total dose of radiation per three-dimensional image is approximately 80 mrad.

11. A method of imaging an object, the method comprising the steps of:

irradiating the object multiple times, each irradiation being performed at a position angularly displaced from a previous irradiation position, said annular positions being non-uniformly distributed about the object;

detecting radiation transmitted through the object at each of said angular positions to create two-dimensional radiation transmission data; and constructing a three dimensional image of the object by analyzing said transmission data;

wherein the step of irradiating the object comprises selecting each irradiation dose to be sufficiently low such that total dose of radiation per three-dimensional image is approximately 80 mrad.

12. A method of imaging an object, comprising the steps of:

irradiating the object from a plurality of non-uniformly distributed angular positions;

detecting radiation transmitted through the object for each of said angular positions at a different spatial resolution to create a two-dimensional radiation transmission data; and constructing a three-dimensional image of the object by analyzing said transmission data.

13. A method of imaging an object, the method comprising the steps of:

irradiating the object multiple times, each irradiation being performed at a position angularly displaced from a previous irradiation position, said angular positions being non-uniformly distributed about the object;

detecting radiation transmitted through the object at each of said angular positions at a different spatial resolution to create a two-dimensional radiation transmission data; and constructing a three-dimensional image of the object by analyzing said radiation transmission data.

* * * * *